United States Patent

Keller et al.

Patent Number: 5,865,856
Date of Patent: Feb. 2, 1999

[54] 2,5-DIAMINOBENZONITRILE COMPOUNDS AND OXIDATION HAIR DYE COMPOSITIONS CONTAINING SAME

[75] Inventors: Helmut Keller, Darmstadt; Wolfgang Balzer, Alsbach, both of Germany

[73] Assignee: Wella Aktiengesellschaft, Darmstadt, Germany

[21] Appl. No.: 819,523

[22] Filed: Mar. 17, 1997

[30] Foreign Application Priority Data

Mar. 29, 1996 [DE] Germany .................. 196 12 506.5

[51] Int. Cl.$^6$ ............... A61K 7/13; C07C 255/50
[52] U.S. Cl. ............ 8/410; 8/407; 8/408; 8/411; 8/412; 8/416; 8/603; 8/649; 558/418
[58] Field of Search ................. 8/406, 408, 410, 8/411, 412, 416, 603, 649, 407; 558/418

[56] References Cited

U.S. PATENT DOCUMENTS

| 5,032,138 | 7/1991 | Wolfram et al. | 8/410 |
| 5,139,532 | 8/1992 | Chan et al. | 8/405 |
| 5,304,014 | 4/1994 | Wenke | 8/408 |
| 5,609,651 | 3/1997 | Mager et al. | 8/406 |

FOREIGN PATENT DOCUMENTS

| 0 299 497 | 7/1988 | European Pat. Off. . |
| 0 391 662 | 4/1990 | European Pat. Off. . |
| 25 25 250 | 12/1975 | Germany . |
| WO 93/13079 | 7/1993 | WIPO . |
| WO 94/27564 | 5/1997 | WIPO . |

*Primary Examiner*—Paul Lieberman
*Assistant Examiner*—Caroline D. Liott
*Attorney, Agent, or Firm*—Michael J. Striker

[57] ABSTRACT

The oxidation hair dye composition is based on a combination of coupler substance and developer substance, and includes, as developer substance, at least one 2,5-diaminobenzonitrile compound of the formula (I),

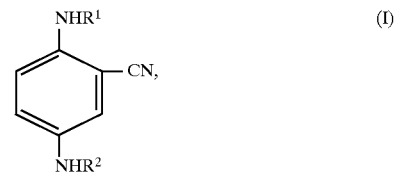

in which $R^1$ and $R^2$, independently of each other, are selected from the group consisting of H, alkyl groups having 1 to 6 carbon atoms, hydroxyalkyl groups having 2 to 4 carbon atoms and dihydroxyalkyl groups having 3 to 4 carbon atoms, with the proviso that both of the $R^1$ and $R^2$ groups are not both hydrogen at the same time, or a physiologically compatible water-soluble salt thereof. The invention also includes new 2,5-diaminobenzonitrile compounds of formula I.

12 Claims, No Drawings

2,5-DIAMINOBENZONITRILE COMPOUNDS AND OXIDATION HAIR DYE COMPOSITIONS CONTAINING SAME

BACKGROUND OF THE INVENTION

The present invention relates to an oxidation hair dye composition for dyeing hair based on a combination of developer substance and coupler substance, which contains at least one 2,5-diaminobenzonitrile compound and also to new 2,5-diaminobenzonitrile compounds.

Oxidation hair dye compounds have achieved a predominant position in the field of hair dyeing. The colors of the dyed hair arise by reaction of certain developer substances with certain coupler substances in the presence of suitable oxidizing agents.

Particularly 2,5-diaminotoluene, 2,5-diaminophenylethyl alcohol, p-aminophenol and 1,4-diaminobenzene are used as developers substances. Resorcinol, 4-chlororesorcinol, 1-naphthol, 3-aminophenol and derivatives of m-phenylenediamine are used as the coupler substance.

Oxidation hair dye compounds used on human hair have many special requirements. They must be unobjectionable in regard to toxicological and dermatological properties and provided a dyed hair color of the desired color intensity. Furthermore a satisfactory light-, permanent wave-, acid and friction resistance is required of the hair colors obtained in the dyeing process. In every case the hair color of the dyed hair must remain stable for at least 4 to 6 weeks despite the action to of light, friction and chemical agents. Moreover a broad pallete of different color shades may be produced by an appropriate combination of suitable developer and coupler substances.

With the current hair dye compositions however it is not possible to fulfill all aspects of the above-mentioned requirements, particularly since problems exist for the developer substances.

SUMMARY OF THE INVENTION

It is an object of the present invention to provide an oxidation hair dye composition based on a suitable combination of developer and coupler substances, particularly an oxidation hair dye composition which fulfills the above-mentioned requirements in an outstanding manner.

It has now been found that an oxidation hair dye composition based on a combination of coupler and developer substances which contains a 2,5-diaminobenzonitrile compound of the formula (I),

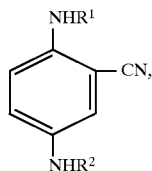

in which $R^1$ and $R^2$, independently of each other, are selected from the group consisting of H, alkyl groups having 1 to 6 carbon atoms, hydroxyalkyl groups having 2 to 4 carbon atoms and dihydroxyalkyl groups having 3 to 4 carbon atoms, with the proviso that both $R^1$ and $R^2$ are not both hydrogen at the same time, or a physiologically compatible water-soluble salt thereof, as the developer substance satisfies the above-mentioned requirements in an outstanding manner.

The 5-amino-2-methylaminobenzonitrile, 5-amino-2-(2'-hydroxyethyl)aminobenzonitrile, 5-amino-2-(2',3'-dihydroxypropyl)aminobenzonitrile, 2-amino-5-(2'-hydroxyethyl)aminobenzonitrile and 2-amino-5-(2',3'-dihydroxypropyl)aminobenzonitrile and their hydrochloride salts are particularly preferred as the 2,5-diaminobenzoenitrile compound of the formula I.

The hair dye composition according to the invention should contain the developer substance of formula (I) generally in amounts of from 0.01 to 5.0 percent by weight, preferably in amounts of from 0.1 to 3.5 percent by weight.

Although the advantageous properties of the developer substances of formula I described here are obtained when these substances are used as the sole developer substance, it is understandably also possible to use the developer substances of formula I together with known developer substances, such as 1,4-diaminobenzene, 2,5-diaminotoluene, 2,5-diaminophenylethyl alcohol, 4-aminophenol, 4-amino-3-methylphenol, 4,5-diaminopyrazole derivatives or tetraaminopyrimidines.

The coupler substances advantageously may be 1-naphthol, resorcinol, 4-chlororesorcinol, 2-methylresorcinol, 2-amino-4-(2'-hydroxy-ethyl)amino anisole, 2,4-diamino-5-ethoxytoluene, 4,6-dichlororesorcinol, m-phenylenediamine, 5-amino-2-methylphenol, 2,4-diaminophenoxyethanol, 4-amino-2-hydroxyphenoxyethanol, 3-aminophenol, 3-amino-2-methylphenol, 4-hydroxy-1,2-methylene-dioxybenzene, 4-amino-1,2-methylenedioxybenzene, 4-(2'-hydroxy-ethyl)amino-1,2-methylenedioxybenzene, 2,4-diamino-5-fluorotoluene, 3-amino-4-chloro-6-methylphenol, 3-amino-2-chloro-6-methylphenol, 3-amino-4-fluoro-6-methyhlphenol, 4-hydroxyindole, 3-amino-4-methoxy-6-methylphenol or 3,5-diamino-2,6-dimethoxypyridine. These coupler compounds may be present in amounts from about 0.01 to 5.0 percent by weight, advantageously from 0.1 to 2.5 percent by weight.

The coupler and developer substances can be added to the hair dye composition according to the invention individually or in a mixture with each other.

The total amount of the developer and coupler substances in the hair dye composition described here can amount to from 0.02 to 10.0 percent by weight, but a total amount of developer and coupler substances in the range from 0.2 to 6.0 percent by weight is particularly preferred. The developer component may generally be present in about an equimolar amount with respect to the coupler component, but either the developer component or the coupler component may be in excess with respect to the other component.

The hair dye composition according to the invention can also include other dyeing ingredients, for example, 6-amino-2-methylphenol, 2-amino-5-methylphenol and conventional direct-dyeing dye compounds, e.g. triphenylmethane dye compounds, such as 4-[(4'-aminophenyl)-(4'-imino-2",5"-cyclohexadien-1"-yliden)-methyl]-2-methyaminobenzene monohydrochloride (C.I. 42 510) and 4-[(4'-amino-3'-methylphenyl)-(4"-imino-3"-methyl-2",5"-cyclohexadien-1"-yliden)-methyl]-2-methyl-aminobenzene monohydrochloride (C.I. 42 520), aromatic nitro dye compounds such as 4-(2'-hydroxyethyl)amino-3-nitrotoluene, 2-amino-4,6-dinitrophenol, 2-amino-5-(2'-hydroxyethyl)aminonitrobenzene and 1-[(2'-ureido-ethyl)amino]-4-nitrobenzene, azo dye compounds such as 6-[(4'-aminophenyl)azo]-5-hydroxynaphthalene-1-sulphonic acid sodium salt (C.I. 14 805) and disperse dyestuffs, such as 1,4-diaminoanthraquinone and 1,4,5,8-tetraaminoanthraquinone. These other hair dye compounds can be contained in the hair dye composition according to the invention in amounts of about 0.1 to 4.0 percent by weight.

Understandably the coupler substance and the developer substance as well as the other dye compounds, in so far as they are bases, can also be in the form of their physiologically compatible salts with organic or inorganic acids, e.g. hydrochloric or sulphuric acid, or—in so far as they have aromatic hydroxy group—in the form of their salts with bases, e.g. alkali phenolates.

Furthermore the hair dye composition according to the invention can contain additional conventional cosmetic additives, for example antioxidants such as ascorbic acid, thioglycolic acid or sodium sulfite, perfume oils, complex formers, wetting agents, emulsifiers, thickeners and hair care substances.

The form of the hair dye composition according to the invention can be, e.g., a solution, especially an aqueous or aqueous-alcoholic solution. Preferably, however, the hair dye composition is in the form of a creme, a gel or an emulsion. Its composition includes a mixture of the hair dye compounds with the additives normally used in such preparation.

The conventional additives used in the solutions, cremes, emulsions or gels include, e.g., solvents such as water, lower aliphatic alcohols, for e.g. ethanol, propanol or isopropanol, glycerol or glycols such as 1,2-propylene glycol; wetting agents or emulsifiers from the classes of anionic, cationic, amphoteric or nonionic surfactant compounds such as fatty alcohol sulfates, ethoxylated fatty alcohol sulfates, alkylsulfonates, alkylbenzene sulfonates, alkyltrimethylammonium salts, alkylbetaines, ethoxylated fatty alcohols, ethoxylated nonylphenols, fatty acid alcoholamides and ethoxylated fatty acid esters; thickeners such as higher fatty alcohols, starches, cellulose derivatives, petrolatum, paraffin oils and fatty acids as well as hair care substances such as cationic resins, lanolin derivatives, cholesterol, pantothenic acid and betaine. The above-mentioned ingredients are used in amounts suitable for their purposes, e.g. the wetting agents and emulsifiers in concentrations of about 0.5 to 30 percent by weight, the thickeners in an amount of about 0.1 to 25 percent by weight and the hair care substances in concentrations of about 0.1 to 5.0 percent by weight.

According to its ingredients, the hair dye composition according to the invention can be weakly acidic, neutral or alkaline. Particularly it can have a pH value from 6.8 to 11.5. The pH maybe adjusted advantageously by addition of ammonia, but also organic amines, e.g. monoethanolamine and triethanolamine, or also inorganic bases, such as sodium hydroxide and potassium hydroxide, can be used. For pH adjustment in the acid range, e.g., phosphoric acid, acetic acid or other organic acids, such as citric acid or tartaric acid can be used.

For oxidative dyeing of hair the above-described hair dye composition is mixed with an oxidizing agent immediately prior to use and the mixture is applied to the hair in an amount sufficient for the dyeing treatment according to the amount of the hair, generally about 60 to 200 grams.

Primarily hydrogen peroxide, or its addition compound with urea, melamine, sodium borate or sodium carbonate, in the form of a 3 to 12%, advantageously 6%, aqueous solution can be used as oxidizing agent for the development of a hair color. However, also air oxygen can be used. If a 6% hydrogen peroxide is used as the oxidizing agent, the weight ratio of hair dye composition to oxidizing agent is from 5 to 1 to 1 to 2, advantageously however 1 to 1. Greater amounts of oxidizing agent are used primarily with higher dye concentration of hair dye compounds or when simultaneously a strong bleaching of the hair is required. The mixture is allowed to act on the hair for about 10 to 45 minutes, advantageously 30 minutes, at 15° to 5020 C.; then the hair is rinse with water and dried. If necessary the hair is subsequently washed with the shampoo and eventually rinsed with a weak organic acid, e.g. citric acid or tartaric acid. Subsequently the hair is dried.

The 2,5-diaminobenzonitriles of formula (I) contained in the hair dye composition according to the invention may, for example, be prepared according to the following reaction schema by catalytic hydrogenation of a suitable 2-amino-5-nitrobenzonitrile (III a) or 5-amino-2-nitrobenzonitrile (III b) (in which R has the same significance as $R^1$ and $R^2$)

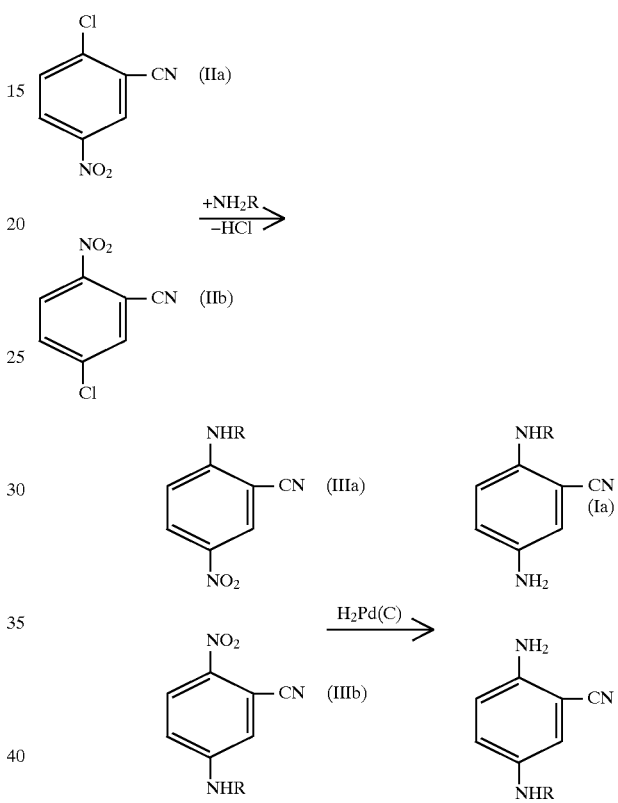

The amino group can be necessarily alkylated in the 2- and/or 5-position.

The subject matter of the present invention also includes new 2,5-diaminobenzonitrile compounds of the formula (I). The 5-amino-2-methylaminobenzonitrile, 2-amino-5-(2'-hydroxyethyl) aminobenzonitrile, 2-amino-5-(2',3'-dihydroxypropyl)aminobenzonitrile, 5-amino-2-(2'-hydroxyethyl)aminobenzonitrile and 5-amino-2-(2',3'-dihydroxypropyl)aminobenzonitrile are particularly preferred.

The compounds of formula (I) can be used both as free bases and also in the form of their physiologically compatible salts with inorganic or organic acids, such as hydrochloric acid, sulfuric acid, phosphoric acid, acetic acid, propionic acid, lactic acid or citric acid. The compounds of formula (I) are soluble in water and have outstanding storage stability, especially as components or ingredients of the hair dye composition described here.

The hair dye composition according to the invention which contains a 2,5-diaminobenzonitrile of the formula (I) as developer substance provides dyed hair colors having outstanding stability, especially to light, washing and friction.

In regard to their dyeing properties the hair dye compositions of the invention provide a broad pallette of different color shades for the dyed hair according to their type and composition. Colors for the dyed hair which can be obtained include blonds, browns, purples, violet to blue shades and black. These colors are particularly characterized by their outstanding color intensities.

The excellent dyeing properties of the hair dyeing composition according to the present invention permit the dyeing of gray, chemically not previously damaged hair without problems and with good color coverage.

The following examples should illustrate the present invention in more detail, but should not be considered as limiting the claims appended hereinbelow.

EXAMPLES

Production Examples

Example 1
Synthesis of 2-alkylamino-5-nitrobenzonitrile
General Method:

18.25 g (0.1 mol) 2-chloro-5-nitrobenzonitrile are dissolved in 50 ml of ethanol. Subsequently 0.22 mol of the corresponding amine are added under reflux. After ending the reaction the solvent is distilled off by vacuum rotary evaporator and the residue mixed with 150 ml ice water. The precipitate obtained is filtered off, washed twice with 50 ml ice water and then dried.

1a. 2-methylamino-5-nitrobenzonitrile
Amine used: methylamine
Yield: 16.3 g (=92 percent of theoretical)
Melting point: 180° C. (yellow crystals).

1b. 2-(2'-hydroxyethyl)amino-5-nitrobenzonitrile
Amine used: 2-hydroxyethylamine
Yield: 19.8 g (=96 percent theoretical)
Melting point: 158° C. (yellow crystals).

1c. 2-(2',3'-dihydroxypropyl) amino-5-nitrobenzonitrile
Amine used: 2,3-dihydroxypropylamine
Yield: 21.2 g (=89 percent theoretical)
Melting point: 144° C. (yellow crystals).

Example 2
Synthesis of 5-alkylamino-2-nitrobenzonitrile
General method:

18.25 g (0.1 mol) 5-chloro-2-nitrobenzonitrile are dissolved in 50 ml of ethanol. Subsequently 0.22 mol of the corresponding amine are added under reflux. After ending the reaction the solvent is distilled off in a rotary evaporator and the residue mixed with 150 ml of ice water. The precipitate obtained is filtered off, washed twice with 50 ml of ice water and then dried.

2a. 5-(2'-hydroxyethyl)amino-2-nitrobenzonitrile
Amine used: 2-hydroxyethylamine
Yield: 18.3 g (=88 percent of theory)
Melting point: 116° C. (yellow crystals)

2b. 5-(2',3'-dihydroxypropyl)amino-2-nitrobenzonitrile
Amine used: 2,3-dihydoxypropylamine
Yield: 20.5 g (85 percent of theoretical)
melting point: 136° C. (yellow crystals)

Example 3
Synthesis of 2-alkylamino-5-aminobenzonitriles and 5-alkylamino-2-aminobenzonitrile
General method:

10 mmol alkylaminonitrobenzonitrile according to example 1 or 2 are dissolved in 50 ml ethanol and are hydrogenated under addition of 50 mg of a palladium-activated carbon catalyst (10%) at 50° C. After uptake of the required amount of hydrogen, the product is filtered from the catalyst and mixed with an excess of dilute hydrochloride acid. After concentrating the resulting solution in a rotary evaporator, the precipitated hydrochloride salt is filtered off and dried.

3a. 5-amino-2-methylaminobenzonitrile hydrochloride
Melting point: 230° C. (decomposed): colorless crystals
CHN Analysis:

| $(C_8H_{10}N_3Cl)$ | % C | % H | % N |
| --- | --- | --- | --- |
| Theoretical: | 52.32 | 5.49 | 22.88 |
| Found: | 52.49 | 5.53 | 22.75 |

3b. 5-amino-2-(2'-hydroxyethyl)aminobenzonitrile hydrochloride
Melting point: 153° C. (decomposed): colorless crystals
CHN Analysis:

| $(C_9H_{12}N_3OCl)$ | % C | % H | % N |
| --- | --- | --- | --- |
| Theoretical | 50.59 | 5.66 | 19.67 |
| Found: | 49.98 | 5.74 | 19.67 |

3c. 5-amino-2-(2',3'-dihydroxypropyl)aminobenzonitrile hydrochloride
Melting point: 135° C. (decomposed): colorless crystals
CHN Analysis:

| $(C_{10}H_{14}N_3O_2Cl)$ | % C | % H | % N |
| --- | --- | --- | --- |
| Theoretical | 49.28 | 5.79 | 17.25 |
| Found: | 49.15 | 5.96 | 17.08 |

3d. 2-amino5-(2'-hydroxyethyl)aminobenzonitrile hydrochloride
Melting point: 160° C. (decomposed): colorless crystals
CHN Analysis:

| $(C_9H_{12}N_3OCl)$ | % C | % H | % N |
| --- | --- | --- | --- |
| Theoretical | 50.59 | 5.66 | 19.67 |
| Found: | 50.05 | 6.02 | 18.90 |

3e. 2-amino-5-(2',3'-dihydroxypropyl)aminobenzonitrile hydrochloride
Melting point: 130° C. (decomposed): colorless crystals
CHN Analysis:

| $(C_{10}H_{14}N_3O_2Cl)$ | % C | % H | % N |
| --- | --- | --- | --- |
| Theoretical | 49.28 | 5.79 | 17.25 |
| Found: | 49.25 | 5.77 | 17.75 |

EXAMPLES OF HAIR DYE COMPOSITIONS

Examples 4 to 15

General prescription for ingredients of examples 4 to 15: 0.0025 mol developer according to Table 1

0.0025 mol coupler according to Table 1

25.0 g oleic acid 10.0 g ammonia (22% aqueous solution)

7.0 g isopropanol 0.3 g ascorbic acid ad water to 100.0 g 50 g of the above-described hair dye solution are mixed shortly prior to use with 50 g of a 6 percent hydrogen peroxide solution and the mixture is then applied to bleached hair. After an acting time of 30 minutes at 40° C. the hair is rinsed with water, washed with a commercially available shampoo and dried. The particular developer and coupler substances and the result of the dyeing procedure using them are summarized in Table I.

TABLE I

Dyed Hair Color resulting from use of the Hair Dyeing Compositions According to the Invention

| Example | Developer/Coupler | Color |
|---|---|---|
| 4 | 2,5-diaminobenzonitrile.HCl/<br>2-amino-4-(2'-hydroxyethyl)-<br>aminoanisole sulfate | Blue-violet |
| 5 | 2,5-diaminobenzonitrile.HCl/<br>5-amino-2-methylphenol | Bright red |
| 6 | 5-amino-2-methylaminobenzonitrile.HCl/<br>2-amino-4-(2'-hydroxyethyl)amino-<br>anisole sulfate | dark blue-violet |
| 7 | 5-amino-2-methylaminobenzonitrile.HCl/<br>5-amino-2-methylphenol | red |
| 8 | 5-amino-2-(2'-hydroxyethyl)amino-<br>benzonitrile.HCl/<br>2-amino-4-(2'-hydroxyethyl)amino-<br>anisole sulfate | dark blue-violet |
| 9 | 5-amino-2-(2'-hydroxyethyl)amino-<br>benzonitrile.HCl/<br>5-amino-2-methylphenol | red |
| 10 | 5-amino-2-(2'-hydroxyethyl)amino-<br>benzonitrile.HCl/<br>m-aminophenol | brown-rose |
| 11 | 5-amino-2-(2'-hydroxyethyl)amino-<br>benzonitrile.HCl/<br>resorcinol | dark blond |
| 12 | 5-amino-2-(2',3'-dihydroxypropyl)-<br>aminobenzonitrile.HCl/<br>2-amino-4-(2'-hydroxyethyl)amino-<br>anisole sulfate | dark blue-violet |
| 13 | 5-amino-2-(2',3'-dihydroxypropyl)amino-<br>benzonitrile.HCl/<br>5-amino-2-methylphenol | red |
| 14 | 5-amino-2-methylphenol<br>2-amino-5-(2'-hydroxyethyl)amino-<br>benzonitrile.HCl/ | rose |
| 15 | 5-amino-2-methylphenol<br>2-amino-5-(2',3'-dihydroxypropyl)amino<br>benzonitrile.HCl/<br>m-aminophenol | blond/rose |

| Example 16: | Hair Dye Composition in Creme form |
|---|---|
| 3.33 g | 5-amino-2-methylaminobenzonitrile hydrochloride |
| 1.50 g | resorcinol |
| 1.40 g | 2-amino-4-(2'-hydroxyethyl)amino anisole sulfate |
| 0.70 g | m-aminophenol |
| 15.00 g | cetyl alcohol |
| 3.50 g | sodium lauryl alcohol diglycol ether sulfate (28 percent aqueous solution) |
| 3.00 g | ammonia (25% aqueous solution) |
| 0.30 g | sodium sulfite, water-free |
| 71.27 g | water |
| 100.00 g | |

50 g of this hair dye composition are mixed with 50 ml hydrogen peroxide solution (6 percent) immediately prior to use. Subsequently the mixture is applied to natural blond hair and allowed to act for 30 minutes at 40° C. After that the hair is rinsed with water and dried. The hair is dyed a black color.

| Example 17: | Hair Dye Composition in Creme form |
|---|---|
| 0.07 g | 5-amino-2-(2'-hydroxyethyl)aminobenzonitrile hydrochloride |
| 0.37 g | resorcinol |
| 0.11 g | 2-methylresorcinol |
| 0.04 g | 4-amino-2-methylphenol |
| 0.07 g | 2-amino-6-chloro-4-nitrophenol |
| 15.00 g | cetyl alcohol |
| 3.50 g | sodium lauryl alcohol diglycol ether sulfate (28 percent aqueous solution) |
| 3.00 g | ammonia (25% aqueous solution) |
| 0.30 g | sodium sulfite, water-free |
| 77.54 g | water |
| 100.00 g | |

50 g of this hair dye composition are mixed with 50 ml hydrogen peroxide solution (6 percent) immediately prior to use. Subsequently the mixture is applied to natural blond hair and allowed to act for 30 minutes at 40° C. After that the hair is rinsed with water and dried. The hair is dyed a fashionable golden brown color.

Unless indicated otherwise, all percentages are in percentages by weight.

We claim:

1. An oxidation hair dye composition comprising at least one coupler substance and at least one developer substance, said at least one developer substance including a 2,5-diaminobenzonitrile compound of the formula (I),

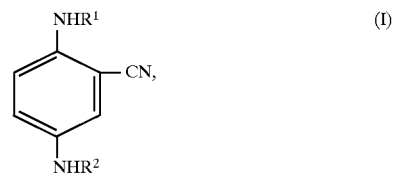

in which $R^1$ and $R^2$, independently of each other, are selected from the group consisting of H, alkyl groups having 1 to 6 carbon atoms and dihydroxyalkyl groups having 3 to 4 carbon atoms, with the proviso that both of said $R^1$ and $R^2$ are not both hydrogen at the same time, or a physiologically compatible water-soluble salt thereof.

2. The hair dye composition as defined in claim 1, wherein said at least one developer substance is selected from the group consisting of 5-amino-2-methylaminobenzonitrile, 5-amino-2-(2',3'-dihydroxypropyl)aminobenzonitrile, 2-amino-5-(2',3'-dihydroxypropyl)aminobenzonitrile and hydrochloride salts thereof.

3. The hair dye composition as defined in claim 1, containing from 0.01 to 5.0 percent by weight of said at least one developer substance.

4. The hair dye composition as defined in claim 1, wherein said at least one coupler substance is selected from the group consisting of 1-naphthol, resorcinol, 4-chlororesorcinol, 2-methylresorcinol, 2-amino-4-(2'-hydroxyethyl)aminoanisole, 2,4-diamino-5-ethoxytoluene, 4,6-dichlororesorcinol, m-phenylenediamine, 5-amino-2-methylphenol, 2,4-diaminophenoxyethanol, 4-amino-2-hydroxyphenoxyethanol, 3-aminophenol, 3-amino-2-methylphenol, 4-hydroxy-1,2-methylenedioxybenzene, 4-amino-1,2-methylenedioxybenzene, 4-(2'-hydroxyethyl)amino-1,2-methylenedioxybenzene, 2,4-diamino-5-fluorotoluene, 3-amino-4-chloro-6-methylphenol, 3-amino-2-chloro-6-methylphenol, 3-amino-4-fluoro-6-methyhlphenol, 4-hydroxyindole, 3-amino-4-methoxy-6-methylphenol and 3,5-diamino-2,6-dimehoxypyridine.

5. The hair dye composition as defined in claim 1, containing from 0.02 to 10.0 percent by weight of a total amount of said at least one developer substance and said at least one coupler substance.

6. The hair dye composition as defined in claim 1, containing from 0.01 to 5.0 percent by weight of said at least one developer substance and from 0.01 to 5.0 percent by weight of said at least one coupler substance.

7. The hair dye composition as defined in claim 1, further comprising at least one dye compound selected from the group consisting of 6-amino-2-methylphenol, 2-amino-5-methylphenol, 4-((4'-aminophenyl)-(4'-imino-2",5"-cyclohexadien-1"-yliden)-methyl)-2-methyaminobenzene monohydrochloride, 4-((4'-amino-3'-methylphenyl)-(4"-imino-3"-methyl-2",5"-cyclo-hexadien-1"-yliden)-methyl)-2-methyl-aminobenzene monohydrochloride, 4-(2'-hydroxyethyl)amino-3-nitrotoluene, 2-amino-4,6-dinitrophenol, 2-amino-5-(2'-hydroxyethyl)aminonitrobenzene, 1-(2'-ureidoethyl)amino-4-nitrobenzene, 6-((4'-aminophenyl)azo)-5-hydroxynaphthalene-1-sulphonic acid sodium salt, 1,4-diaminoanthraquinone and 1,4,5,8-tetraaminoanthraquinone.

8. The hair dye composition as defined in claim 7, containing from 0.1 to 4.0 percent by weight of said at least one dye compound.

9. A 2,5-diaminobenzonitrile compound of the formula (I),

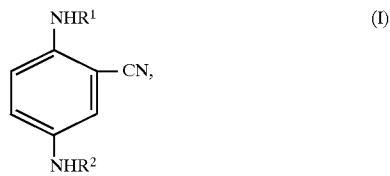

in which $R^1$ and $R^2$, independently of each other, are selected from the group consisting of H, alkyl groups having 1 to 6 carbon atoms and dihydroxyalkyl groups having 3 to 4 carbon atoms, with the proviso that both of said $R^1$ and $R^2$ are not both hydrogen at the same time, or a physiologically compatible water-soluble salt thereof.

10. The 2,5-diaminobenzonitrile as defined in claim 9 and consisting of 5-amino-2-methylaminobenzonitrile.

11. The 2,5-diaminobenzonitrile as defined in claim 9 and consisting of 2-amino-5-(2',3'-dihydroxypropyl)aminobenzonitrile.

12. The 2,5-diaminobenzonitrile as defined in claim 9 and consisting of 5-amino-2-(2',3'-dihydroxypropyl)aminobenzonitrile.

* * * * *